United States Patent
Ita et al.

(10) Patent No.: US 6,537,318 B1
(45) Date of Patent: Mar. 25, 2003

(54) USE OF GLUCOMANNAN HYDROCOLLOID AS FILLER MATERIAL IN PROSTHESES

(75) Inventors: Essien Eyo-Okon Ita, South River, NJ (US); Scott Hilton Clarke, Plantation, FL (US)

(73) Assignee: Konjac Technologies, LLC, South River, NJ (US)

( * ) Notice: Subject to any disclaimer, the term of this patent is extended or adjusted under 35 U.S.C. 154(b) by 529 days.

(21) Appl. No.: 09/055,472

(22) Filed: Apr. 6, 1998

(51) Int. Cl.⁷ .................................................. A61F 2/00
(52) U.S. Cl. ......................................... 623/11.11; 623/8
(58) Field of Search .............................. 623/7, 8, 9, 11, 623/12, 16, 66, 901; 424/422, 423; 426/96, 573, 578; 128/898

(56) References Cited

U.S. PATENT DOCUMENTS

| | | | | |
|---|---|---|---|---|
| 3,928,322 A | * | 12/1975 | Sugiyama et al. | 260/236.5 |
| 4,138,382 A | * | 2/1979 | Polmanteer | 260/29.6 |
| 4,455,691 A | * | 6/1984 | Van Aken Redinger et al. | 3/36 |
| 5,019,096 A | | 5/1991 | Fox, Jr. et al. | |
| 5,082,663 A | * | 1/1992 | Konishi et al. | 424/445 |
| 5,282,857 A | * | 2/1994 | Perry et al. | 623/8 |
| 5,308,636 A | * | 5/1994 | Tye et al. | 426/573 |
| 5,324,531 A | * | 6/1994 | Hoefler et al. | 426/573 |
| 5,344,451 A | | 9/1994 | Dayton | |
| 5,364,520 A | * | 11/1994 | Okuyama et al. | 204/299 R |
| 5,462,761 A | * | 10/1995 | McGinley et al. | 426/573 |
| 5,486,364 A | * | 1/1996 | King et al. | 424/488 |
| 5,531,786 A | * | 7/1996 | Perry et al. | 623/8 |
| 5,571,183 A | | 11/1996 | Kazem et al. | |
| 5,624,612 A | * | 4/1997 | Sewall et al. | 264/4.1 |
| 5,658,329 A | * | 8/1997 | Purkait | 623/11 |

FOREIGN PATENT DOCUMENTS

| | | |
|---|---|---|
| GB | 2164343 | 3/1986 |
| JP | 01288269 | * 9/1993 |
| JP | 04027427 | * 10/1993 |

* cited by examiner

*Primary Examiner*—David J Isabella
(74) *Attorney, Agent, or Firm*—Gibbons, Del Deo, Dolan, Griffinger & Vecchione

(57) ABSTRACT

A prosthetic device for implantation into a mammalian body comprised of a non-absorbable biocompatible flexible material shell or sac filled with various biocompatible gel filler materials. The gel filler materials are comprised of biocompatible glucomannan obtained from konjac hydrocolloid flour and other biocompatible hydrocolloids, producing a natural look and feel for the prosthetic implants, especially reconstructive prostheses such as breast implants.

9 Claims, No Drawings

USE OF GLUCOMANNAN HYDROCOLLOID AS FILLER MATERIAL IN PROSTHESES

BACKGROUND OF THE INVENTION

1. Field of the Invention

The present invention relates to a reconstructive surgical implant device, more particularly to a device useful as a prosthesis such as a breast implant. The present invention is biocompatible and natural in look and feel.

2. Background of the Invention

The implantation of reconstructive prosthetic devices is a commonly elected surgical procedure performed for cosmetic or reconstructive purposes, such as post-mastectomy breast reconstruction. In the past, in breast augmentation or reconstruction procedures, it was conventional to use either saline solutions or silicone gels as filler material. The drawbacks of the prior art procedures, especially the use of silicone, has been the cause of growing concern.

The use of silicone gels in prostheses, and especially in reconstructive prostheses such as breast prostheses involves a number of drawbacks and hazards. There is evidence that silicone gel inadvertently may leak into the body which may cause a number of adverse immune effects. The production of antibodies and, in some cases, inflammatory reactions has necessitated the removal of the implant. In addition, leakage of silicone into the body has been linked to scleroderma, eye trouble and rheumatism. Litigation surrounding silicone filled breast implants has reached enormous levels.

Saline fillers produce a rather unusual look and feel and often slowly leak or deflate over time. Also such fillers have a relatively low resistance to changes in ambient pressure.

Soy bean oil fillers have also been developed. These are particularly resistant to the onset of infection from bacterial and other biological impurities. However, soy bean oil fillers are more likely to leak and do not look and feel as natural as the prostheses of the present invention.

It is the object of this invention to provide a new filler material which will overcome the problems associated with many prior art filler materials. The present invention makes use of a readily available, biocompatible material as the prosthesis filler.

SUMMARY OF THE INVENTION

The present invention comprises a non-absorbable, flexible material shell or sac filled with biocompatible gel filler material. More particularly, the invention relates to the use of glucomannon hydrocolloid, obtained from konjac flour, combined with another hydrocolloid as a filler for prosthetic implants, especially reconstructive prostheses such as breast implants. The konjac flour-containing gel fillers of the present invention present a number of advantages over other fillers heretofore utilized in the area. They are biocompatible, unlikely to leak, and also have a natural look and feel.

DETAILED DESCRIPTION OF THE INVENTION

As set forth above, the present invention is a novel surgical device suitable for implanting in a human. The implant comprises a non-absorbable flexible material shell or sac filled with biocompatible gel filler material. The container or sac of the present invention is made of flexible, non-absorbable material. Suitable materials for this purpose include polymers well known in the art, including natural rubber, polybutadiene, cellulose acetate, cellulose acetate butyrate, cellulose nitrate, cross-linked polyvinyl alcohol, polyurethane, nylon, polyvinyl acetate, polyvinyl butyrate, ethylene-vinyl acetate copolymers, polyethylene and polypropylene. etc. Preferably, the sac is made of non-absorbable silicone rubber material.

The biocompatible gel filler material used in the present invention is comprised of konjac and another biocompatible hydrocolloid. Konjac is the generic name for the flour formed from grinding the root of the konjac plant. Konjak flour is a high molecular weight, non-starch polysaccharide classified as glucomannan. The glucomannan molecule is the functional component of konjac. The molecular structure is comprised of glucose and mannose chains in a ratio of 1 to 1.6 respectively. Glucomannan has short side branches and acetyl groups randomly present at the C-6 position of a sugar unit. Glucomannan molecules have a molecular weight between about 200,000 daltons and about 2,000,000 daltons and are typically about 1,000,000 daltons.

The acetyl groups associated with the konjac glucomannan inhibit the molecules from forming a gel network. Introducing mild alkalies known in the art to a konjac solution cleaves the acetyl groups and results in a strong elastic gel which retains its structure under various heat conditions including boiling water, microwave heating and retort processing.

In addition to its gelling and thickening properties, konjac is synergistic with certain other hydrocolloids and starches. The synergistic effect increases the strength and elasticity of the gel. Konjac forms very strong gels in combination with carrageenan, xanthan bean gum and locust bean gum. The gels are formed by heating and cooling combinations of these synergistic hydrocolloids and starches with konjac and may be made thermally stable by deacetylating the konjac glucomannon molecule using heat and/or addition of an alkali as described above. Konjac interacts with most starches to produce an increase in viscosity.

Konjac-carrageenan gels, konjac-starch gels and konjac-xanthan gels are all suitable fillers for the prosthesis of the present invention . Soy bean oil or another biocompatible trigyceride may be added to the filler to safeguard against the onset of infection.

NUTRICOL® (FMC Corporation—Philadelphia, Pa.; Brussels, Belgium; Singapore) konjac gels are examples of commercially available suitable filler materials contemplated for use in the present invention implant. In particular, NUTRICOL® GP 751, a high strength konjac-carrageenan gel, is especially suitable due to its biocompatibility and its ability to impart a natural look and feel to the present invention implant. NUTRICOL® GP 650, a konjac/xanthan gum which forms strong elastic gels is also suitable as a filler. Other NUTRICOL® konjac products which are articles of commerce and which are suitable for use as gel fillers in the present invention include NUTRICOL® GP 624, a konjac/carrageenan gel and NUTRICOL® GP 440, a konjac/starch gel.

EXAMPLE

In order to produce a prosthesis according to the present invention with, for example, a 3% gel using a glucomannan/hydrocolloid filler, the following steps are performed in the laboratory:

1. Tare empty stainless steel beaker and add desired water (distilled or sterilized) content (97% by weight).
2. Weigh glucomannan/hydrocolloid blend powder NUTRICOL® GP 650, FMC Corporation - Philadelphia, Pa.;

Brussels, Belgium; Singapore)) at 3% by weight (hereinafter referred to as the blend).
3. Place the stainless steel beaker containing water in a hot water bath.
4. Agitate/stir the water in the beaker with a medium to high shear mixer. Mix at high speed taking care not to let water escape over the sides of the beaker.
5. Slowly add the blend powder and increase mixing speed accordingly.
6. Heat mixture to 185–195° F. and hold for 3 to 5 minutes. Remove from hot water bath and add back any water lost (distilled or sterilized) so that the weight after heating is the same as the initial weight.
7. Immediately deaerate the gel mixture using a deaerator or similar equipment known in the art which will take the air out of the gel solution.
8. Place the warm gel solution into a pre-shaped silicone membrane using a syringe or other method known in the art.
9. After filling the membrane, the prosthesis is sealed with a prosthetically approved silicone glue or other method known in the art and allowed to cool to room temperature.
10. Before implantation, the prosthesis must be sterilized using known medically approved methods.

The gel may contain anywhere from 0.1% to 5% by weight of the blend powder. At step 6 triglycerides may be added if desired to increase infection resistance.

The present invention has been described in the foregoing specification with respect to a specific embodiment. This embodiment serves as an example to illustrate the invention rather than to limit its scope. Modifications may be made thereto without departing from the broader teachings of the invention.

What is claimed is:

1. A prosthesis for implantation in a mammalian body comprising:
   a) a shell made from a flexible, non-absorbable biocompatible material; and
   b) a gel filler material contained within said shell wherein said gel filler material comprises glucomannan.
2. The prosthesis of claim 1 wherein said glucomannan gel filler material is obtained from konjac gel.
3. The prosthesis of claim 2 wherein said konjac gel is a konjac-carrageenan gel.
4. The prosthesis of claim 2 wherein said konjac gel is a konjac-xanthan gum gel.
5. The prosthesis of claim 2 wherein said konjac gel is a konjac-starch gel.
6. The prosthesis of claim 1 wherein said flexible non-absorbable material of said shell is selected from the group consisting of natural rubber, polybutadiene, cellulose acetate, cellulose acetate butyrate, cellulose nitrate, cross-linked polyvinyl alcohol, polyurethane, nylon, polyvinyl acetate, polyvinyl butyrate, ethylene vinyl acetate copolymers polyethylene, polypropylene and non-absorbable silicone material.
7. A method of making a prosthesis for implanation into a mammalian body which comprises filling a shell made from flexible, non-absorbable biocompatible material with a filler material comprising glucomannan.
8. The method of claim 7 wherein said shell and said filler material are sterilized.
9. The method of claim 7 wherein said shell is filled with a filler material consisting of 3% by weight biocompatible konjac-xanthan gum filler material and 97% by weight water.

* * * * *